(12) United States Patent
Wang et al.

(10) Patent No.: US 7,887,861 B2
(45) Date of Patent: Feb. 15, 2011

(54) TOPICAL PREPARATIONS COMPRISING FLOWER WAX AND CANDELILLA

(75) Inventors: Tian Xiang Wang, Dix Hills, NY (US); Paul Marotta, Farmingdale, NY (US); Katie Ann Frampton, West Babylon, NY (US); Robert Mou, Stony Brook, NY (US)

(73) Assignee: ELC Management LLC, New York, NY (US)

( * ) Notice: Subject to any disclaimer, the term of this patent is extended or adjusted under 35 U.S.C. 154(b) by 17 days.

(21) Appl. No.: 12/160,449

(22) PCT Filed: Jan. 19, 2007

(86) PCT No.: PCT/US2007/060742

§ 371 (c)(1),
(2), (4) Date: Apr. 3, 2009

(87) PCT Pub. No.: WO2007/084972

PCT Pub. Date: Jul. 26, 2007

(65) Prior Publication Data

US 2009/0324756 A1 Dec. 31, 2009

(51) Int. Cl.
*A61K 36/73* (2006.01)
*A61K 36/752* (2006.01)
*A61K 36/53* (2006.01)
*A61K 36/00* (2006.01)

(52) U.S. Cl. .................. 424/765; 424/736; 424/745; 424/725; 424/778

(58) Field of Classification Search .................. None
See application file for complete search history.

(56) References Cited

U.S. PATENT DOCUMENTS

| 5,587,174 A | 12/1996 | Lang et al. |
| 6,153,196 A | 11/2000 | Kripp et al. |
| 2002/0164293 A1 * | 11/2002 | Barone et al. ............... 424/64 |

FOREIGN PATENT DOCUMENTS

JP 59-021608 2/1984

OTHER PUBLICATIONS

Lipstick Facts. Knight Ridder Tribune News Service. Washington. Dec. 5, 2001. p. 1 (p. 1-2 in ProQuest).*
Penny Smith. Petal Power How rose-scented beauty has grown back into fashion. Daily Mail. London (UK): Aug 17, 2000. p. 44 (pp. 1-3 in ProQuest).*
Waxes; http://www.cyberlipd.org/wax/wax0001.htm; Accessed Dec. 15, 2005.

* cited by examiner

*Primary Examiner*—Christopher R Tate
*Assistant Examiner*—Melenie McCormick
(74) *Attorney, Agent, or Firm*—Peter Giancana

(57) ABSTRACT

The invention pertains to topical, wax-based compositions comprising one or more flower waxes and candelilla wax, in the ratio of about 20:1 to about 1:20. Such compositions may have improved shear resistance or be substantially plasticizer free. Stick-type and stay-in-place topical preparations are contemplated.

7 Claims, No Drawings

TOPICAL PREPARATIONS COMPRISING FLOWER WAX AND CANDELILLA

FIELD OF THE INVENTION

The present invention pertains to improved topical skin and hair care preparations, in particular, compositions comprising one or more flower waxes in specified proportion with conventional wax, especially candelilla wax.

BACKGROUND

The use of waxes in cosmetic and dermatologic preparations is well known. Natural waxes in cosmetic formulation are solid or semi-solid mixtures of hydrocarbons, often used to confer or increase structure in a liquid matrix. They are also used to modify hardness, brittleness, flow and melt characteristics. Applied to the skin or hair, waxes create a water repellant film and therefore confer emolliency to those compositions in which a wax is deployed. Wax is not a chemically precise term. The substances to which the term is applied are, generally, malleable and hydrophobic and have a melting point above about 45° C. Chemically, waxes are lipids and may be esters of ethylene glycol (ethan-1,2-diol) and two fatty acids or they may be esters of a fatty acid with a fatty alcohol.

The most common cosmetic waxes are animal, mineral, vegetable or petroleum-derived. Synthetic waxes are also known and used in the cosmetics industry. Among animal derived waxes, beeswax is by far the most common and may act as a "reference" wax, while lanolin (wool wax) and spermaceti (from the sperm whale) have also been used in skin preparations. Okorite and ceresin are among the naturally occurring mineral waxes. Carnauba, candelilla and castor are well known cosmetic waxes of the vegetable type. Carnauba is the hardest natural wax and has the highest melting range (78-85° C.). Paraffins and microcrystalline waxes are among those derived from petroleum that also find use in the skin care field.

Structure vs. Payoff

The choice of which wax or blend of waxes to use depends, in part, on the amount of structure that must be imparted to the finished product. In turn, that amount of structure depends on the type of product and how the product is to be used and applied. A product with too much structure may not have good payoff or deposit on the surface being treated. That is it may take many applications to get a substantial amount of product onto the treated surface.

On the other hand, a product with too little structure, while having good payoff, is susceptible to smearing, either during or after application. It should also be understood that the majority of cosmetic and dermatologic products lose structure when sheared. Thus, when designing topical preparations it is necessary to consider the degree of shearing to which a product may be subjected up to the moment of application to the treated surface. A product that has a good amount of structure shortly after it is manufactured may lose structure by the time the product is applied by a consumer. The trick is to get to the consumer a product that still has an effective amount of structure, while providing good payoff.

When discussing shear, one has to understand thixotropy. Thixotropy refers to the property of some materials to exhibit a time-dependent change in structure (and viscosity) as a result of applied shear. By time dependent, it is meant that the longer the material undergoes shear, the greater the material's loss of structure and the lower its viscosity. Thus, in a product that is subject to shear by drawing across the skin, like lipstick, the product gets less viscous the longer it is used and that causes the payoff to be inconsistent. Thus, in getting to the consumer a product with an effective amount of structure and a consistent payoff, it is advantageous to develop products that have a time-independent response to shear, or as little time dependence as possible. From a structure point of view, products with lesser thixotropy are preferred.

Plasticizers

Products based on relatively hard waxes (high structure) confront the problem of poor payoff, by adding plasticizers to the formulation. In a conventionally executed formulation, the plasticizer softens the wax and improves payoff or deposit. Plasticizers, however, have drawbacks. For example, plasticizers may be irritating to the skin of a user. Also, plasticizers are chemically very different from the waxes on which they are intended to act. Therefore, conventional plasticizers introduce into the product, a foreign component having nothing to do with the real purpose of the product. What would be better is if the payoff of hard wax compositions could be improved by an additive that is much closer, chemically, to the base wax.

Flower Wax

Throughout the specification, "flower wax" refers to a substance obtained from any part of a flowering plant. For example, the wax may reside near the reproductive structure, on the leaves or on the fruit of the flowering plant. In practice, flower waxes are often obtained as a by-product of an essential oil extraction process. Some flower waxes useful in the present invention include, but are not limited to: apple, bitter orange, chamomile, jasmine, lavender, mimosa, narcissus, raspberry, rose and violet.

Flower waxes, as separate from the term "conventional waxes", have found limited use in topical preparations. Flower waxes have not been used in stick products because conventional implementation leads to end products that lack sufficient structure immediately following manufacture, and made worse by subsequent shearing. For example, in lipstick, substitution of flower waxes for all of the conventional waxes renders the lipstick incapable of withstanding the necessary applied force. In use, the stick breaks or simply mashes when drawn (sheared) across the lips. Furthermore, flower waxes have not been used in stay-in-place products. By "stay-in-place" product we mean a product or portion thereof that remains atop the surface of the skin or hair, that does not evaporate or volatilize away, that is visible to the human eye and that generally requires mechanical force to remove. In cosmetics, many pigmented make-ups fit this definition. For example, stay-in-place product like mascara or foundation, made by substituting flower waxes for all of the conventional waxes, smudges too easily, during and after application.

On the other hand, compositions made with flower wax have relatively good deposit on skin and hair, in particular, brush-on mascara and hair products. Likewise, flower wax stick products (i.e. lipsticks and lip balms) have relatively good payoff onto the skin or lips. By "deposit" and "payoff," we mean the amount of product transferred to a surface, regardless of the quality of the application. Also, flower waxes in general have a pleasant, fragrant component, while many waxes have no odor or even malodor. In any number of situations the fragrant component of flower wax would be considered a positive aspect of the material. Also, flower waxes are chemically more similar to conventional waxes than other additives, and the combination of flower waxes with conventional waxes is less likely to create compatibility problems. Thus it would be desirable to take advantage of one or more beneficial properties of flower wax, if the structure problem associated with flower wax could be mitigated. Unknown in the prior art is a method of rendering flower wax-based compositions less susceptible to shear.

PRIOR ART

U.S. Pat. No. 5,587,174 discloses compositions for conditioning and cleansing skin and hair. These skin and hair treatment composition includes 0.5 to 2 percent by weight of apple wax, 0.1 to 30 percent by weight of at least one anionic, cationic, amphoteric and/or nonionic surfactant, a solvent consisting of water, ethanol, propanol, isopropanol, glycols or mixtures thereof and one or more cosmetic additives selected from the group consisting of perfume oils; opacifiers; pearlescing agents; bacterial and fungicidal ingredients; coconut fatty acid diethanolamide; buffer substances; coloring materials; solubilizers; light stabilizers; antioxidants; complexing agents and antidandruff active ingredients. Regarding candelilla and carnauba wax, this reference discloses some of their shortcomings by saying, "these waxes are hard and brittle, have a high melting point and are difficult to emulsify in conventional cosmetic compositions". The combination of one or more of flower waxes with candelilla wax is not disclosed and, in fact, is taught against. The specific benefits of the combination of flower wax and candelilla wax is not disclosed nor suggested. Furthermore, some of the compositions disclosed are substantially liquid, meaning that the compositions do not support shear and are therefore, not within the scope of the present invention.

U.S. Pat. No. 6,153,196 discloses the use of flower wax, preferably from jasmine, mimosa, narcissus, bitter orange or wild chamomile in liquid hair treatment products, as replacements for candelilla wax. The flower waxes are said to be "similar to all natural plant waxes . . . having hydrophobic properties, such as melting and emulsifying properties and biodegradability". However, flower waxes appear to have a " . . . high absorption rate into hair. Even minimal concentrations already have a marked conditioning effect on the hair. In addition, a significant luster and a marked neutralization of worked-in fragrances can be noticed in the cosmetic hair preparations. In addition, a liquid hair treatment agent containing flower wax is distinguished by its dermatological compatibility, its good moisturizing capacity and its oil-restoring effect, e.g. in hair cleansing lotions. These effects are achieved when the liquid hair treatment agent has a flower wax content in a quantity of 0.001 to 20 weight-percent, preferably in a quantity of 0.01 to 12 weight-percent, and particularly preferably in a quantity of 0.03 to 2 weight-percent". In relation to candelilla wax, this reference notes, "that by exchanging carnauba or candelilla wax in the basic formula with each of the aforementioned flower waxes, an improvement in combability was obtained". Also, "The foam conditioner creates a silky foam and improves the combability and the texture of the hair washed with it," this last quote referring to example 4 in which candelilla wax had been replaced by each flower wax, jasmine, mimosa, bitter orange and narcissus. The point is that this reference specifically teaches the replacement of candelilla wax with one or more flower waxes. The combination of one or more of flower waxes with candelilla or carnauba wax is not disclosed and, in fact, is taught against. The benefits of specific combinations of flower wax and candelilla wax is not disclosed nor suggested. Furthermore, some of the compositions disclosed are substantially liquid, meaning that the compositions do not support shear and are therefore, not within the scope of the present invention.

JP 59-021608 (abstract only) purports to disclose a jasmine flower wax "having improved compatibility with raw materials for cosmetic, improved hydrating properties, emulsification properties, providing cosmetic with a particle size and gloss". In addition to jasmine wax, compositions contain a nonpolar hydrocarbon, polar ester, alcohol and fatty acid. Disclosed is a hair stick comprising 10.0 wt % jasmine wax, 10.0 wt % Japanese wax, 10.0 wt % bees wax, a proper amount of perfume, a proper amount of dyestuff, and a proper amount of antiseptic. The combination of one or more of flower waxes with candelilla or carnauba wax is not disclosed and, in fact, is taught against. The benefits of specific combinations of flower wax and candelilla wax is neither disclosed nor suggested.

Candelilla wax has been described as follows.

"This wax is produced by small shrubs from Mexico, *Euphorbia cerifera* and *E. antisyphilitica* (Euphorbiaceae). The wax is extracted by boiling the plant (to separate the wax and the plant material). The wax floats to the top of the water and is skimmed off and processed. It contains hydrocarbons (about 50% of C29 to C33), esters (28-29%), alcohols, free fatty acids (7-9%), and resins (12-14% triterpenoid esters). Its melting point is 67-79° C. It has been used mainly mixed with other waxes to harden them without raising the melting point. This wax is used in cosmetics (lip balms and lotion bars), pharmaceutics and in food stuffs (E 902, GRAS) to improve stability and texture as a substitute to beeswax (melting point: 66-71° C.). One of candelilla's major outlets was a binder for chewing gums." (*Waxes*, http://www.cyberlipd.org/wax/wax0001.htm; accessed Dec. 15, 2005)

OBJECT

A main object of the present invention is to provide stick-type and stay-in-place topical preparations comprising flower wax as the dominant wax, the compositions having improved structure and improved performance under shear.

Another object of the invention is to provide stick-type and stay-in-place topical preparations comprising a conventional wax base (preferably candelilla), but no conventional plasticizer.

SUMMARY

The present invention covers stick-type and stay-in-place topical preparations comprising one or more flower waxes in combination with one or more conventional waxes in the ratio from 20:1 to 1:20. The foregoing includes compositions comprising a conventional wax base (preferably candelilla), wherein one or more flower waxes is substituted for some or all conventional plasticizer. The foregoing also includes compositions comprising a flower wax base, wherein candelilla wax is included in an amount sufficient to yield a shear resistant composition.

DETAILED DESCRIPTION

Throughout this specification, the terms "comprise," "comprises," "comprising" and the like shall consistently mean that a collection of objects is not limited to those objects specifically recited. Furthermore, regarding compositions according to the present invention, all recitations of percent levels are to be understood as being "about" that level, unless otherwise noted.

Throughout this specification the term "shear resistant" means that a composition has a relatively low thixotropy or that a composition loses less structure as a result of shearing.

Candelilla wax is a vegetable derived wax, coming from the Mexican shrubs *Euphorbia cerifera* and *Euphorbia antisyphilitica*. It has been unexpectedly found, especially in view of the prior art, that the combination of flower wax and, in particular, candelilla wax, substantially solves the insufficient structure problem of flower waxes, while unexpectedly yielding compositions of relatively low thixotropy. It has been further noted that combinations of flower wax and other conventional waxes do not have the same low thixotropy effect as the combination of flower wax and candelilla wax, which seems to be a unique benefit of candelilla wax.

That flower wax in combination with candelilla wax solves the structure and strength problems of flower wax is no where disclosed in the prior art and even goes against the teachings of U.S. Pat. No. 5,587,174 and U.S. Pat. No. 6,153,196. Specifically, as mentioned above, U.S. Pat. No. 5,587,174 suggests that, in topical preparations, candelilla wax should not be combined with flower wax. And U.S. Pat. No. 6,153,196 specifically teaches that flower waxes are superior to candelilla wax in liquid hair products and therefore flower waxes should be used without candelilla wax. In light of this, the inventors have not only gone against the suggestions of the prior art, but in so doing have discovered a useful effect seemingly specific to candelilla wax. The article discussed above, entitled "Wax", does say that "It [candelilla wax] has been used mainly mixed with other waxes to harden them without raising the melting point." However, hardness implies nothing specific about shear response and nothing at all about the time dependence of the shear response. Many materials are hard, yet shear easily. Furthermore, the present invention does not directly mix candelilla wax with flower wax to harden the flower wax. The present invention concerns topical compositions comprising both flower wax and candelilla wax. The waxes are generally separately added to a composition, so that candelilla wax is not mixed with flower wax and may not harden the flower wax, which, at any rate, is not the effect sought. However, when one of the effects sought is an increase in overall hardness of some compositions that comprise flower wax (not a specific hardening of the flower wax, but of the overall composition), this may also be achieved with candelilla wax.

The inventors have unexpectedly found that the separate addition of flower wax and candelilla wax imparts properties to a topical preparation that are not imparted by combinations of flower waxes and other non-flower waxes, for example, carnauba and paraffin. The following shear studies (results in table 2) demonstrate that mascaras made with flower and candelilla waxes, behave differently than mascaras made with flower and carnauba waxes or flower and paraffin waxes. Standard definitions of rheological terms are somewhat application dependent, but those found in the following reference may be useful to the reader: "Guide To Rheological Nomenclature Measurements In Ceramic Particulate Systems;" National Institutes of Standards and Technology Special Publication 946, January 2001; herein, incorporated by reference, in its entirety.

A standard rheometric test is a variable rate shear tests that characterizes the behavior of a material over a range of applied shear. The test generates a graph wherein the rate of applied shear is plotted on a horizontal axis and the stress induced in the test mascara is plotted on a vertical axis. Starting from zero, shear is increased over a defined range, here 0 to 1000 sec$^{-1}$. As the shear increases, so too does the stress in the sample, recorded in the graph as dynes per centimeter square. When the upper limit shear rate has been reached, the rate of shear is decreased in a controlled manner back to zero and the stress measured along the way. The entire test may take as little as two minutes. In a graph produced by this kind of test, "up curves" represent the induced stress as shear is being ramped up and "down curves" track the stress as the shear is being ramped down. The fact that a down curve does not exactly retrace the up curve is indicative of "thixotropic" behavior in the test sample, and the area between the curves provides a measurement of the degree of thixotropy.

This test was performed for each of three mascara compositions given in table 1. All three compositions comprised lavender flower wax (4.8%) and raspberry leave wax (0.2%). These measurements were conducted at ambient conditions (25° C.) using a standard parallel steel plate geometry, the plate having a diameter of 2.0 cm and a 200 micron gap. The test duration was 2.0 minutes, one minute ramping the shear up and one minute ramping the shear down. The ramp mode was linear and continuous.

TABLE 1

| Material | Composition 1 | Composition 2 | Composition 3 |
| --- | --- | --- | --- |
| water | 43.08 | 43.08 | 43.08 |
| iron oxides | 10.00 | 10.00 | 10.00 |
| acrylates copolymer | 9.00 | 9.00 | 9.00 |
| glyceryl stearate | 4.80 | 4.80 | 4.80 |
| stearic acid | 4.80 | 4.80 | 4.80 |
| calcium aluminum borosilicate | 3.50 | 3.50 | 3.50 |
| silica | 4.70 | 4.70 | 4.70 |
| polyisobutene | 3.50 | 3.50 | 3.50 |
| oleic acid | 2.40 | 2.40 | 2.40 |
| aminomethyl propanediol | 1.60 | 1.60 | 1.60 |
| PVP polycarbamyl polyglycol ester | 1.17 | 1.17 | 1.17 |
| caprylyl glycol/ phenoxyethanol/ hexylene glycol | 1.00 | 1.00 | 1.00 |
| hydroxyethylcellulose | 0.70 | 0.70 | 0.70 |
| ethylhexylglycerine | 0.50 | 0.50 | 0.50 |
| Disodium EDTA | 0.20 | 0.20 | 0.20 |
| phenoxyethanol | 0.15 | 0.15 | 0.15 |
| simethicone | 0.10 | 0.10 | 0.10 |
| hexylene glycol | 0.10 | 0.10 | 0.10 |
| hinokitiol | 0.10 | 0.10 | 0.10 |
| rice bran wax | 0.10 | 0.10 | 0.10 |
| lavender flower wax | 4.80 | 4.80 | 4.80 |
| raspberry leaf wax | 0.20 | 0.20 | 0.20 |
| candelilla wax | 3.50 | — | — |
| carnauba wax | — | 3.50 | — |
| paraffin wax | — | — | 3.50 |

The following thixotropy was measured.

TABLE 2

| "Conventional" wax in the composition | Thixotropy (area between up and down curves—dyne/cm$^2$ sec) | Percent change compared to candelilla wax composition |
| --- | --- | --- |
| candelilla | 170,000 | — |
| carnauba | 610,000 | 259% |
| paraffin | 1,071,000 | 530% |

Thixotropy is a measure of the time dependent breakdown of the composition in shear. The smaller the thixotropy, the lesser the time dependence and the greater the ability of the composition to maintain its structure under shear. As can be seen in table 2, when candelilla wax is replaced by carnauba wax or paraffin wax, the time dependence increases dramatically. It can be expected that for a given exposure to shearing forces, the carnauba composition and the paraffin composition will suffer far more structure breakdown than the candelilla composition. Furthermore, its smaller thixotropy also indicates that compositions comprising flower and candelilla wax will recover from the effects of shearing faster than the other two. The result of this is that flower wax based stick compositions and stay-in-place compositions, having commercially acceptable properties (structure and payoff), are possible when candelilla wax is used, but not carnauba or paraffin. The composition with flower wax and candelilla is significantly more shear resistant then the compositions with flower wax and carnauba or paraffin. Furthermore, it is possible to produce commercially suitable compositions with flower waxes and candelilla wax as the only wax components of the composition. For example, absent other waxes, suitable flower wax-based compositions are possible wherein the ratio of flower wax to candelilla wax ranges from about 20:1 to about 1:1 and wherein the candelilla wax comprises no more than about 10% of the total composition, by weight.

Flower Wax vs. Plasticizer in Candelilla-Based Compositions

It will now be further appreciated that, due to their true wax nature, flower waxes may be employed as a substitute for plasticizers, in wax based compositions. In conventional waxy compositions, plasticizers may comprise as much as about 10% or more of the total weight of the composition and there is always a concern that, at certain levels, conventional plasticizers will cause user irritation in a topical composition. Irritation may be alleviated by substituting some or all of the plasticizer with flower wax. Again, the focus here is not on a direct mixture of two waxes. Rather, the use of flower wax corrects or alleviates a problem in conventional wax-based compositions. Also, the flower wax has greater compatibility with the non-flower, wax base, than does a conventional plasticizer. The benefit of flower wax over conventional plasticizer is particularly true in candelilla-based compositions, as now discussed.

In candelilla-based compositions, at least some flower waxes perform better than conventional plasticizers, meaning that some amount of plasticizer can be replaced with a lesser amount of flower wax. To demonstrate this, a lipstick wire test was conducted. Test parameters were as follows: wire speed 0.20 mm·sec; attachment TA26 wire cutter; instrument TA XT Plus by Stable Micro System. Results are shown in table 3.

TABLE 3

| Material | Maximum force (gf) | % change |
| --- | --- | --- |
| Candelilla Wax 100% | 1,565.872 | — |
| Candelilla Wax 90%, Permethyl 106 10% | 1,324.614 | −15 |
| Candelilla Wax 90%, Raspberry Wax 10% | 950.218 | −39 |
| Candelilla Wax 90%, Lavender Wax 10% | 937.534 | −40 |

Candelilla wax was tested by itself as a standard. Separately, Permethyl 106, raspberry wax and lavender wax were blended with candelilla and measured. Permethyl 106 (a liquid plasticizer) lowers the maximum cutting force by about 15% over straight candelilla wax. However, the semi-solid flower waxes lower the maximum cutting force by about 39 to 40%, significantly more than the Permethyl 106, even though the Permethyl 106 is a liquid and the waxes are semi-solid. These results are unexpected and suggest the usefulness of compositions comprising candelilla wax and one or more flower waxes in a ratio of about 10:1 to about 1:1. Such compositions may also comprise conventional plasticizers or may be substantially free of conventional plasticizer. Conventional plasticizers include those listed in the "Functions" section of Tenth Edition of the International Cosmetic Ingredient Dictionary and Handbook, herein incorporated by reference.

We have previously seen that compositions comprising flower wax and candelilla wax, in a ratio of about 20:1 to about 1:1, can have relatively and unexpectedly low thixotropy and therefore greater shear resistance. Now, we see that flower wax may be used in place of some or all plasticizer, and that the ratio candelilla wax to flower wax may range from about 10:1 to about 1:1. Taken together, the foregoing has demonstrated the unexpected usefulness of compositions comprising one or more flower waxes and candelilla wax, in a ratio of about 20:1 to about 1:10. Flower waxes that have proved useful include waxes obtained from jasmine (for example, *jasminum officinale*), lavender (i.e. *lavendula angustifolia*), rose (i.e. *rosa damascene*), raspberry (i.e. *rubus idaeus*), violet (i.e. *viola odorata*), and orange blossom.

What is claimed is:

1. A topical, wax-based shear resistant composition comprising flower waxes and candelilla wax, in the ratio of about 20:1 to about 1:10, wherein the flower waxes present in the composition include the waxes of jasmine, lavender, rose, raspberry and violet.

2. A composition according to claim 1 further comprising bitter orange wax.

3. A composition according to claim 1 wherein the flower waxes and candelilla wax are in a ratio of about 20:1 to about 1:1.

4. A composition according to claim 3 having no additional wax.

5. A composition according to claim 1 that is substantially plasticizer free.

6. A composition according to claim 5 wherein the candelilla wax and flower waxes are in a ratio of about 10:1 to about 1:1.

7. A composition according to claim 6 having no additional wax.

* * * * *